United States Patent
Schubert et al.

(10) Patent No.: US 7,910,732 B2
(45) Date of Patent: Mar. 22, 2011

(54) METHOD FOR PRODUCING POROUS METAL-ORGANIC FRAMEWORK MATERIALS

(75) Inventors: Markus Schubert, Ludwigshafen (DE); Michael Hesse, Worms (DE); Ulrich Mueller, Neustadt (DE); Hermann Puetter, Neustadt (DE); Markus Tonigold, Blaustein (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 671 days.

(21) Appl. No.: 11/915,499

(22) PCT Filed: May 22, 2006

(86) PCT No.: PCT/EP2006/062488
§ 371 (c)(1),
(2), (4) Date: Nov. 26, 2007

(87) PCT Pub. No.: WO2006/125761
PCT Pub. Date: Nov. 30, 2006

(65) Prior Publication Data
US 2008/0214806 A1    Sep. 4, 2008

(30) Foreign Application Priority Data

May 24, 2005   (DE) .......................... 10 2005 023 856

(51) Int. Cl.
*C07F 15/00* (2006.01)
*C07F 11/00* (2006.01)

(52) U.S. Cl. ................ 544/226; 544/225; 546/2; 549/3; 549/207; 205/424; 205/426; 205/427; 205/440

(58) Field of Classification Search .................. 544/225, 544/226; 546/2; 549/3, 207; 205/424, 426, 205/427, 440
See application file for complete search history.

(56) References Cited

U.S. PATENT DOCUMENTS

| | | |
|---|---|---|
| 3,964,983 A | 6/1976 | Eisenbach et al. |
| 5,648,508 A | 7/1997 | Yaghi |
| 2003/0148165 A1 | 8/2003 | Muller et al. |
| 2003/0222023 A1 | 12/2003 | Mueller et al. |

FOREIGN PATENT DOCUMENTS

| | | |
|---|---|---|
| WO | WO 02/088148 A1 | 11/2002 |
| WO | WO 2005/049892 A1 | 6/2005 |

OTHER PUBLICATIONS

K. Seki, et al., "Syntheses and Characterization of Microporous Coordination Polymers with Open Frameworks", Journal of Physics Chemistry, XP002410884, vol. 106, Jul. 1, 2002, pp. 1380-1385.
Mohamed Eddaoudi, et al., "Systematic Design of Pore Size and Functionality in Isoreticular MOFs and Their Application in Methane Storage", WWW.SCIENCEMAG.ORG, Science, vol. 295, Jan. 18, 2002, pp. 469-472.
Banglin Chen, et al., "Interwoven Metal-Oraganic Framework on a Periodic Minimal Surface with Extra-Large Pores", WWW.SCIENCEMAG.ORG, Science, vol. 291, Feb. 9, 2001, pp. 1021-1023.
Susumu Kitagawa, et al., "Functional Porous Coordination Polymers", Angewandte Chem. Inst. Ed., vol. 43, 2004, pp. 2334-2375.
U.S. Appl. No. 12/594,604, filed Oct. 5, 2009, Stein, et al.
U.S. Appl. No. 12/597,616, filed Oct. 26, 2009, Schubert, et al.
U.S. Appl. No. 12/601,022, filed Nov. 20, 2009, Schubert, et al.

*Primary Examiner* — Porfirio Nazario Gonzalez
(74) *Attorney, Agent, or Firm* — Oblon, Spivak, McClelland, Maier & Neustadt, L.L.P.

(57) ABSTRACT

The present invention relates to processes for preparing a porous metal-organic framework comprising at least two organic compounds coordinated to at least one metal ion, the porous metal-organic frameworks prepared by the process and their use, in particular for gas storage and gas separation.

15 Claims, No Drawings

METHOD FOR PRODUCING POROUS METAL-ORGANIC FRAMEWORK MATERIALS

This application is a 371 of PCT/EP2006/062488, filed May 22, 2006.

The present invention relates to processes for preparing porous metal-organic frameworks, the frameworks obtained in this way and their use.

Crystalline porous metal-organic frameworks (MOFs) having particular pores or pore distributions and large specific surface areas have in recent times in particular become the object of comprehensive research work.

Thus, for example, U.S. Pat. No. 5,648,508 describes microporous metal-organic frameworks which are prepared from a metal ion and a ligand in the presence of a template compound under mild reaction conditions.

WO-A 02/088148 discloses the preparation of a series of compounds which have the same framework topology. These IRMOF (isoreticular metal-organic framework) structures are monocrystalline and mesoporous frameworks which have a very high storage capacity for gases.

Eddaoudi et al., Science 295 (2002), 469-472, describe, for example, the preparation of an MOF-5, in which a zinc salt, viz. zinc nitrate, is used as starting material and this salt and 1,4-benzenedicarboxylic acid (BDC) are dissolved N,N'-diethylformamide (DEF) to synthesize the MOF material.

Chen et al., Science 291 (2001), 1021-1023, describe, for example, the preparation of an MOF-14, in which a copper salt (copper nitrate) is used as starting material and this salt and 4,4',4"-benzene-1,3,5-triyltribenzoic acid ($H_3BTC$) are dissolved in N,N'-dimethylformamide (DMF) and water to synthesize the MOF.

To improve the properties of metal-organic frameworks prepared in this way, Seki et al., J. Phys. Chem. B 2002, 106, 1380-1385, have reacted metal-organic frameworks prepared in a conventional way with triethylenediamine in a heterogeneous reaction, Here, the results presented are intended to lead to the development of porous materials in which it is necessary to control the structure for applications such as gas storage, separation, catalysis and molecular recognition.

Similar structures are described by S. Kitagawa et al., Angew, Chem. Int. Ed. 43 (2004), 2334-2375

A further, improved process for preparing new metal-organic frameworks is disclosed in WO-A 2005/049892. Here, metal-organic frameworks are prepared by an electrochemical route and it is in this way possible, despite the use of known metal ion-ligand combinations, to obtain new frameworks which have larger specific surface areas than conventionally prepared frameworks.

Despite numerous improved preparative processes for further optimized and sometimes new metal-organic frameworks, there is still a need to provide processes which are improved compared to these processes.

It is therefore an object of the present invention to provide a process which leads to porous frameworks having improved properties and in particular to provide frameworks which have an increased specific surface area compared to conventionally prepared frameworks.

This object is achieved by a process for preparing a porous metal-organic framework comprising at least two organic compounds coordinated to at least one metal ion, which comprises the step
oxidation of at least one anode comprising metal corresponding to the at least one metal ion in the presence of a first and a second organic compound in a reaction medium, with the first organic compound having at least two carboxylate groups and the at least two organic compounds coordinating to the at least one metal ion.

In addition, the object is achieved by a process for preparing a porous metal-organic framework comprising at least two organic compounds coordinated to at least one metal ion, which comprises the steps:
a) oxidation of at least one anode comprising metal corresponding to the at least one metal ion in the presence of a first organic compound having at least two carboxylate groups which coordinate to the at least one metal ion in a reaction medium to form an intermediate complex comprising the at least one metal ion and the first organic compound;
b) reaction of the intermediate complex at a prescribed temperature with a second organic compound which coordinates to the at least one metal ion.

We have found that the properties of metal-organic frameworks which have been prepared by an electrochemical route and have improved properties compared to conventionally prepared materials can be improved further when the electrochemically produced framework is taken as intermediate complex and reacted again with a further organic compound which likewise coordinates to a metal ion. Furthermore, it has surprisingly been found that new and improved frameworks can likewise be obtained when the abovementioned at least two organic compounds are made available in the reaction medium for the electrochemical preparation and the framework of the invention can thus be produced in one synthesis step.

However, it is not necessary for each metal ion in the porous framework to be coordinated by the second and any further organic compound, whereas each metal ion has to be coordinated by the first organic compound but it is not necessary for each carboxylate group of the first organic compound to be coordinated to one and the same metal ion. Likewise, the second organic compound can coordinate to a plurality of identical or different adjacent metal ions in the framework.

Free coordination sites of the one metal ion or a plurality of different metal ions in the intermediate complex can be occupied by the second organic compound (the second ligand) or partial displacement of the first ligand can occur. A combination of the two variants is likewise conceivable, as long as the preparation is carried out in two steps.

If free coordination sites of one or more different metal ions are occupied by the second ligand, it is possible, for example, for a two-dimensional framework to be formed by linkage of the metal ions of different two-dimensional layers by the second ligand, as is described in J. Phys. Chem. B 2002, 106, 1380-1385.

Intermediate complexes which have a two-dimensional structure are therefore preferred.

In the preparation according to the invention in one synthesis step, comparable mechanisms can occur. Thus, the reaction mechanism can comprise simultaneous incorporation, successive incorporation of the ligands (organic compounds) in the framework or mixed forms thereof.

Step a) of the process of the invention is the anodic oxidation of the at least one metal, with this going as cation into the reaction medium and reacting with a first organic compound to form an intermediate complex. This intermediate complex can, for example, be separated off by filtration and then be reacted further with the second organic compound. It is likewise possible to use the reaction medium employed in step a) in step b), too, with the second organic compound being able to be added as solid or in solution.

Step a) of the process of the invention is preferably carried out as described in WO-A 2005/049892.

In the alternative process of the invention, in which the synthesis is carried out in a single step, the reaction takes place exclusively in the reaction medium for the electrochemical reaction. This can be carried out by a method corresponding to that described in WO-A 2005/049892.

The term "electrochemical preparation" as used in the context of the present invention refers to a method of preparation in which the formation of at least one reaction product is associated with the migration of electric charges or the occurrence of electric potentials.

The term "at least one metal ion" as used in the context of the present invention refers to embodiments in which at least one ion of a metal or at least one ion of a first metal and at least one ion of at least one second metal which is different from the first metal is provided by anodic oxidation.

The present invention accordingly comprises embodiments in which at least one ion of at least one metal is provided by anodic oxidation and at least one ion of at least one metal is provided via a metal salt, with the at least one metal in the metal salt and the at least one metal which is provided as metal ion by means of anodic oxidation being able to be identical or different. The present invention therefore comprises, for example, an embodiment in which the reaction medium comprises one or more different salts of a metal and the metal ion comprised in this salt or in these salts is additionally provided by anodic oxidation of at least one anode comprising this metal. The present invention likewise comprises an embodiment in which the reaction medium comprises one or more different salts of at least one metal and at least one metal which is different from these metals is provided as metal ion by means of anodic oxidation in the reaction medium.

In a preferred embodiment of the present invention, the at least one metal ion is provided by anodic oxidation of at least one anode comprising this at least one metal and no further metal is provided via a metal salt.

The present invention accordingly comprises an embodiment in which the at least one anode comprises a single metal or two or more metals and, when the anode comprises a single metal, this metal is provided by anodic oxidation and when the anode comprises two or more metals, at least one of these metals is provided by anodic oxidation.

Furthermore, the present invention comprises an embodiment in which at least two anodes which can be identical or different are used. Each of the at least two anodes can comprise a single metal or two or more metals. It is possible, for example, for two different anodes to comprise the same metals but in different proportions. It is likewise possible, for example, in the case of different anodes for a first anode to comprise a first metal and a second anode to comprise a second metal, with the first anode not comprising the second metal and/or the second anode not comprising the first metal.

The metal or the metals are elements of groups Ia, IIa, IIIa, IVa to VIIIa and Ib and VIb of the Periodic Table of the Elements. For the purposes of the present invention, further preference is given to Cu, Ni, Fe, Co, Zn, Mn, Ru, Mo, Cr, W, Rh and Pd. Particular preference is given to Cu, Ni and Co. Very particular preference is given to Cu.

Metal ions which can be provided by anodic oxidation in the reaction medium are, in particular, $Cu^{2+}$, $Cu^+$, $Ni^{2+}$, $Ni^+$, $Fe^{3+}$, $Fe^{2+}$, $Co^{3+}$, $Co^{2+}$, $Zn^{2+}$, $Mn^{3+}$, $Mn^{2+}$, $Ru^{3+}$, $Ru^{2+}$, $Mo^{3+}$, $Cr^{3+}$, $W^{3+}$, $Rh^{2+}$, $Rh^+$, $Pd^{2+}$ and $Pd^+$. Particular preference is given to $Cu^{2+}$, $Cu^+$, $Ni^{2+}$, $Ni^+$, $Co^{3+}$ and $Co^{2+}$. Very particular preference is given to $Cu^{2+}$ and $Cu^+$.

The present invention accordingly also describes for step a) or the "single-step synthesis" a process of the type as described above in which a copper- and/or nickel- and/or cobalt-comprising anode is used as metal ion source.

The present invention likewise describes a process of the type described above in which a copper- and/or cobalt-comprising anode is used as metal ion source.

In a preferred embodiment, the present invention also provides a process of the type described above in which a copper-comprising anode is used as metal ion source.

The make-up of the anode used in step a) of the process of the invention or in the "single-step synthesis" can in principle be chosen freely, as long as it is ensured that the at least one metal ion can be made available by anodic oxidation in the reaction medium for formation of the intermediate complex.

Preference is given to, inter alia, anodes in the form of a rod and/or a ring and/or a disk, for example, an annular disk, and/or a plate and/or a tube and/or a bed and/or a cylinder and/or a cone and/or a frustum of a cone.

In a preferred embodiment, the process of the invention is carried out using at least one sacrificial anode in step a) or in the "single-step synthesis". The term "sacrificial anode" as used in the context of the present invention refers to an anode which dissolves at least partly during the course of the process of the invention. Embodiments in which at least part of the dissolved anodic material is replaced during the course of the process are also comprised here. This can, for example, be brought about by at least one new anode being introduced into the reaction system or, in a preferred embodiment, an anode being introduced into the reaction system and being introduced further into the reaction system either continuously or discontinuously during the course of the process of the invention.

The process of the invention is preferably carried out using anodes which consist of the at least one metal serving as metal ion source or comprise this at least one metal applied to at least one suitable support material.

The geometry of the at least one support material is subject to essentially no restrictions. For example, it is possible to use support materials in the form of a woven fabric and/or a thin disk and/or a felt and/or a mesh and/or rod and/or a candle and/or a cone and/or a frustum of a cone and/or a ring and/or a disk and/or a plate and/or a tube and/or a bed and/or a cylinder.

Possible support materials which can be used according to the invention are, for example, metals such as at least one of the abovementioned metals, alloys such as steels or bronzes or brass, graphite, felt or foams.

Very particular preference is given to anodes which consist of the at least one metal serving as metal ion source.

The make-up of the cathode used in step a) of the process of the invention or in the "single-step synthesis" can in principle be chosen freely, as long as it is ensured that the at least one metal ion can be made available by anodic oxidation in the reaction medium for formation of the porous metal-organic framework.

In a preferred embodiment of the process of the invention, the electrically conductive electrode material of the at least one cathode is selected so that no interfering secondary reaction takes place in the reaction medium. Preferred cathode materials are, inter alia, graphite, copper, zinc, tin, manganese, silver, gold, platinum or alloys such as steels, bronzes or brass.

As preferred combinations of the anode material serving as metal ion source and the electrically conductive cathode material, mention may be made, inter alia, for example, of the following:

| Anode | Cathode |
|---|---|
| Zinc | Zinc |
| Copper | Copper |
| Magnesium | Copper |
| Cobalt | Cobalt |
| Iron | Steel |
| Copper | Steel |

The geometry of the at least one cathode is subject to essentially no restrictions. It is possible, for example, to use cathodes in the form of a rod and/or a ring and/or a disk and/or a plate and/or a tube.

For the purposes of the present invention, it is possible to use virtually any of the cell types customary in electrochemistry. In the process of the invention, very particular preference is given to an electrolysis cell which is suitable for use of sacrificial electrodes.

In principle, it is possible inter alia, to use divided cells having, for example, a parallel arrangement of flat electrodes or candle-shaped electrodes. As partition medium between the cell compartments, it is possible to use, for example, ion-exchange membranes, microporous membranes, diaphragms, filter cloths comprising materials which do not conduct electrons, glass frits and/or porous ceramics. Preference is given to using ion-exchange membranes, in particular cation-exchange membranes, among which preference is in turn given to membranes which comprise a copolymer of tetrafluoroethylene and a perfluorinated monomer comprising sulfonic acid groups.

In a preferred embodiment of the process of the invention, one or more undivided cells are preferably used in step a) or in the "single-step synthesis".

The present invention accordingly also provides a process as described above which is carried out in an undivided electrolysis cell.

Very particular preference is given to combinations of geometries of anode and cathode in which the sides of the anode and cathode which face one another together form a gap of homogeneous thickness.

In the at least one undivided cell, the electrodes are, for example, preferably arranged parallel to one another with the electrode gap having a homogeneous thickness in the range from, for example, 0.5 mm to 30 mm, preferably in the range from 0.75 mm to 20 mm and particularly preferably in the range from 1 to 10 mm.

In a preferred embodiment, it is possible, for example, for a cathode and an anode to be arranged parallel to one another so that an electrode gap having a homogeneous thickness in the range from 0.5 to 30 mm, preferably in the range from 1 to 20 mm, more preferably in the range from 5 to 15 mm and particularly preferably in the range from 8 to 12 mm, for example in the region of about 10 mm, is formed in the resulting cell. For the purposes of the present invention, this type of cell will be referred to as a "gap cell".

In a preferred embodiment of the process of the invention, the above-described cell is used as a bipolar cell.

Apart from the above-described cell, the electrodes are employed individually or as a stack of a plurality thereof in a likewise preferred embodiment of the process of the invention. In the latter case, the electrodes are stack electrodes which are preferably connected in series in a bipolar fashion in what is accordingly referred to as a plate stack cell. Particularly when step a) of the process of the invention or the "single-step synthesis" is carried out on an industrial scale, preference is given to using at least one pot cell and particularly preferably plate stack cells connected in series whose in-principle construction is described in DE 195 33 773 A1.

In the preferred embodiment of the plate stack cell, preference is given, for example, to disks of suitable materials, for example copper disks, being arranged parallel to one another so that a gap having a homogeneous thickness in the range from 0.5 to 30 mm, preferably in the range from 0.6 to 20 mm, more preferably in the range from 0.7 to 10 mm, more preferably in the range from 0.8 to 5 mm and in particular in the range from 0.9 to 2 mm, for example in the region of about 1 mm, is formed between each of the individual disks. The distances between the individual disks can be identical or different, and in a particularly preferred embodiment the distances between the disks are essentially identical. In a further embodiment, the material of each disk of the plate stack cell can differ from the material of another disk of the plate stack cell. For example, one disk can be made of graphite and another disk can be made of copper, with the copper disk preferably being connected as anode and the graphite disk preferably being connected as cathode.

For the purposes of the present invention, preference is also given, for example, to using "pencil sharpener" cells as are described, for example, in J. Chaussard et al., J. Appl. Electrochem. 19 (1989) 345-348, whose relevant contents are fully incorporated by reference into the present patent application. Particular preference is given to using pencil sharpener electrodes having rod-shaped electrodes which can be fed in further in the process of the invention.

In particular, the present invention accordingly also provides a process as described above which is carried out in a gap cell or plate stack cell for step a) or for the "single-step synthesis".

Cells in which the electrode spacing is in the region of less than or equal to 1 are referred to as capillary gap cells.

In likewise preferred embodiments of the process of the invention, electrolysis cells having, for example, porous electrodes made up of metal beds or having, for example, porous electrodes made of metal meshes or having, for example, both electrodes made up of metal beds and electrodes made of metal meshes can be used in step a) or in the "single-step synthesis".

In a further preferred embodiment, the process of the invention is carried out using electrolysis cells which have at least one sacrificial anode having a round disk-shaped cross section and at least one cathode having an annular cross section, with the diameter of the preferably cylindrical anode particularly preferably being smaller than the internal diameter of the cathode and the anode being installed in the cathode in such a way that a gap having a homogeneous thickness is formed between the external cylindrical surface of the anode and the interior surface of the cathode which at least partly surrounds the anode.

For the purposes of the present invention, it is also possible to reverse the polarity so as to make the original anode the cathode and the original cathode the anode. In this process variant, it is possible, for example, to choose electrodes comprising different metals so that one metal is firstly anodically oxidized to make it available as metal cation for formation of the metal-organic framework and, in a second step after reversal of the polarity, a further meta is made available for formation of the meta-organic framework. It is likewise possible to bring about reversal of polarity by application of alternating current.

It is in principle possible to carry out the process batchwise or continuously or in a mixed mode. The process is preferably carried out continuously in at least one flow cell.

The voltages employed in the process of the invention can be matched to the respective at least one metal of the at least one anode serving as metal ion source for the intermediate complex and/or to the properties of the first organic compound and/or, if appropriate, to the properties of the at least one solvent described below and/or, if appropriate, to the properties of the at least one electrolyte salt described below and/or to the properties of the at least one cathodic depolarization compound described below.

In general, the voltages per electrode pair are in the range from 0.5 to 100 V, preferably in the range from 2 to 40 V and particularly preferably in the range from 4 to 20 V Examples of preferred ranges are from about 4 to 10 V and from 10 to 20 V and from 20 to 25 V and from 10 to 25 V and from 4 to 20 V and from 4 to 25 V. The voltage can be constant during the course of the process of the invention or can change continuously or discontinuously during the course of the process.

For example, when copper is anodically oxidized, the voltages are generally in the range from 3 to 20 V, preferably in the range from 3.5 to 15 V and particularly preferably in the range from 4 to 15V.

The current densities occurring in the preparation according to the invention of the porous organic frameworks are generally in the range from 0.01 to 1000 $mA/cm^2$, preferably in the range from 0.1 to 1000 $mA/cm^2$, more preferably in the range from 0.2 to 200 $mA/cm^2$, more preferably in the range from 0.3 to 100 $A/cm^2$ and particularly preferably in the range from 0.5 to 50 $mA/cm^2$.

The amounts of charge (Ah) used in the process of the invention are preferably in the range from 30 to 200% of the amount of charge which is necessary to bind the amount of the preferably used acid equivalents of the first organic compound.

The process of the invention is generally carried out at a temperature in the range from 0° C. to the boiling point of the respective reaction medium or the at least one solvent used, preferably in the range from 20° C. to the boiling point, preferably under atmospheric pressure. It is likewise possible to carry out the process under superatmospheric pressure, with pressure and temperature preferably being chosen so that the reaction medium is preferably at least partly liquid.

In general, the process of the invention is carried out at a pressure in the range from 0.5 to 50 bar, preferably in the range from 1 to 6 bar and particularly preferably at atmospheric pressure.

Depending on the type and state of matter of the constituents of the reaction medium, the electrochemical preparation according to the invention of the intermediate complex in step a) or in the "single-step synthesis" can in principle also be carried out without additional solvent. This is particularly the case when, for example, the first organic compound functions as solvent in the reaction medium. Likewise, in the "single-step synthesis" the second or only the second organic compound can serve as solvent.

It is likewise in principle possible to carry out the process of the invention without use of a solvent, for example in the melt, in which case at least one constituent of the reaction medium is present in the molten state.

In a preferred embodiment of the present invention, the reaction medium comprises at least one suitable solvent in addition to the first organic compound and, if appropriate, to the at least one electrolyte salt and, if appropriate, to the at least one cathodic depolarization compound. Here, the chemical nature and amount of this at least one solvent can be matched to the first organic compound and/or to the at least one electrolyte sat and/or to the at least one cathodic depolarization compound and/or to the at least one metal ion.

Conceivable solvents are in principle all solvents or all solvent mixtures in which the starting materials used in step a) or in the "single-step synthesis" of the process of the invention can be at least partly dissolved or suspended under the reaction conditions, e.g. pressure and temperature, selected. Examples of preferred solvents are, inter alia, water;
alcohols having 1, 2, 3 or 4 carbon atoms, e.g. methanol, ethanol, n-propanol, isopropanol, n-butanol, isobutanol, tert-butanol;
carboxylic acids having 1, 2, 3 or 4 carbon atoms, e.g. formic acid, acetic acid, propionic acid or butanoic acid;
nitrites such as acetonitrile or cyanobenzene;
ketones such as acetone;
at least singly halogen-substituted lower alkanes such as methylene chloride or 1,2-dichloroethane;
acid amides such as amides of lower carboxylic acids, e.g. carboxylic acids having 1, 2, 3 or 4 carbon atoms, for example amides of formic acid, acetic acid, propionic acid or butanoic acid, e.g. formamide, dimethylformamide (DMF), diethylformamide (DEF), t-butylformamide, acetamide, dimethylacetamide, diethylacetamide or t-butylacetamide;
cyclic ethers such as tetrahydrofuran or dioxane;
N-formylamides or N-acetylamides or symmetrical or unsymmetrical urea derivatives of primary, secondary or cyclic amines such as ethylamine, diethylamine, piperidine or morpholine;
amines such as ethanolamine, triethylamine or ethylenediamine;
dimethyl sulfoxide;
pyridine;
trialkyl phosphites and phosphates;

or mixtures of two or more of the abovementioned compounds.

The term "solvent" as used above includes both pure solvents and solvents which comprise small amounts of at least one further compound such as, preferably, water. In this case, the water contents of the abovementioned solvents are in the range up to 1% by weight, preferably in the range up to 0.5% by weight, particularly preferably in the range from 0.01 to 0.5% by weight and in particular in the range from 0.1 to 0.5% by weight. For the purposes of the present invention, the term "methanol" or "ethanol" or "acetonitrile" or "DMF" or "DEF" includes, for example, a solvent which can in each case comprise, particularly preferably, water in an amount of from 0.1 to 0.5% by weight.

Preferred solvents for use in step a) or in the "single-step synthesis" of the process of the invention are methanol, ethanol, acetonitrile, DMF and DEF and mixtures of two or more of these compounds. Very particular preference is given to methanol, ethanol, DMF, DEF and mixtures of two or more of these compounds as solvent.

In a preferred embodiment, at least one protic solvent is used as solvent. This is, inter alia, used particularly when cathodic formation of hydrogen is to be achieved to avoid the redeposition as described below of the at least one metal ion provided by anodic oxidation on the cathode.

When methanol is used as solvent, for example, the temperature in the process of the invention under atmospheric pressure is generally in the range from 0 to 90° C.; preferably in the range from 0 to 65° C. and particularly preferably in the range from 25 to 65° C.

When ethanol is used as solvent, for example, the temperature in the process of the invention under atmospheric pressure is generally in the range from 0 to 100° C.; preferably in the range from 0 to 78° C. and particularly preferably in the range from 25 to 78° C.

The pH of the reaction medium in the process of the invention is set so that it is advantageous for the synthesis or the stability or preferably for the synthesis and the stability of the framework. For example, the pH can be adjusted by means of the at least one electrolyte salt.

If the reaction is carried out as a batch reaction, the reaction time is generally in the range up to 30 hours, preferably in the range up to 20 hours, more preferably in the range from 1 to 10 hours and particularly preferably in the range from 1 to 5 hours.

The first organic compound, which comprises at least two carboxylate groups, is preferably derived from a saturated or unsaturated aliphatic compound or an aromatic compound or a both aliphatic and aromatic compound.

The aliphatic compound or the aliphatic part of the both aliphatic and aromatic compound can be linear and/or branched and/or cyclic, with a plurality of rings per compound also being possible. More preferably, the aliphatic compound or the aliphatic part of the both aliphatic and aromatic compound comprises from 1 to 15, more preferably from 1 to 14, more preferably from 1 to 13, more preferably from 1 to 12, more preferably from 1 to 11 and particularly preferably from 1 to 10, carbon atoms, for example, 1, 2, 3, 4, 5, 6, 7, 8, 9 or 10 carbon atoms. Particular preference is here given to, inter alia, methane, adamantane, acetylene, ethylene or butadiene.

The aromatic compound or the aromatic part of the both aromatic and aliphatic compound can have one or more rings, for example two, three, four or five rings, in which case the rings may be present separately from one another and or at least two rings may be present in fused form. The aromatic compound or the aromatic part of the both aliphatic and aromatic compound more preferably has one, two or three rings, with one or two rings being particularly preferred. Furthermore, each ring of the compound mentioned can independently comprise at least one heteroatom such as N, O, S, B, P, Si, Al, preferably N, O and/or S. More preferably, the aromatic compound or the aromatic part of the both aromatic and aliphatic compound comprises one or two $C_6$ rings, with the two being able to be present separately from one another or in fused form. In particular, mention may be made of benzene, naphthalene and or biphenyl and/or bipyridyl and/or pyridine as aromatic compounds.

Examples which may be mentioned are, inter alia, trans-muconic acid and fumaric acid and phenylenebisacrylic acid.

For the purposes of the present invention, mention may be made, for example of dicarboxylic acids such as
1,4-butanedicarboxylic acid, 4-oxopyran-2,6-dicarboxylic acid, 1,6-hexanedicarboxylic acid, decanedicarboxylic acid, 1,8-heptadecanedicarboxylic acid, 1,9-heptadecanedicarboxylic acid, heptadecanedicarboxylic acid, acetylenedicarboxylic acid, 1,2-benzenedicarboxylic acid, 2,3-pyridinedicarboxylic acid, pyridine-2,3-dicarboxylic acid, 1,3-butadiene-1,4-dicarboxylic acid, 1,4-benzenedicarboxylic acid, p-benzenedicarboxylic acid, imidazole-2,4-dicarboxylic acid, 2-methylquinoline-3,4-dicarboxylic acid, quinoline-2,4-dicarboxylic acid, quinoxaline-2,3-dicarboxylic acid, 6-chloroquinoxaline-2,3-dicarboxylic acid, 4,4'-diaminophenylmethane-3,3'-dicarboxylic acid, quinoline-3,4-dicarboxylic acid, 7-chloro-4-hydroxyquinoline-2,8-dicarboxylic acid, diimidedicarboxylic acid, pyridine-2,6-dicarboxylic acid, 2-methylimidazole-4,5-dicarboxylic acid, thiophene-3,4-dicarboxylic acid, 2-isopropylimidazole-4,5-dicarboxylic acid, tetrahydropyran-4,4-dicarboxylic acid, perylene-3,9-dicarboxylic acid, perylenedicarboxylic acid, Pluriol E 200-dicarboxylic acid, 3,6-dioxaoctanedicarboxylic acid, 3,5-cyclohexadiene-1,2-dicarboxylic acid, octanedicarboxylic acid, pentane-3,3-dicarboxylic acid, 4,4'-diamino-1,1'-diphenyl-3,3'-dicarboxylic acid, 4,4'-diaminodiphenyl-3,3'-dicarboxylic acid, benzidine-3,3'-dicarboxylic acid, 1,4-bis-(phenylamino)-benzene-2,5-dicarboxylic acid, 1,1'-binaphthyl-8,8'-dicarboxylic acid, 7-chloro-8-methylquinoline-2,3-dicarboxylic acid, 1-anilinoanthraquinone-2,4'-dicarboxylic acid, polytetrahydrofuran-250-dicarboxylic acid, 1,4-bis-(carboxymethyl)-piperazine-2,3-dicarboxylic acid, 7-chloroquinoline-3,8-dicarboxylic acid, 1-(4-carboxy)phenyl-3-(4-chloro)phenylpyrazoline-4,5-dicarboxylic acid, 1,4,5,6,7,7-hexachloro-5-norbornene-2,3-dicarboxylic acid, phenylindandicarboxylic acid, 1,3-dibenzyl-2-oxo-imidazolidine-4,5-dicarboxylic acid, 1,4-cyclohexanedicarboxylic acid, naphthalene-1,8-dicarboxylic acid, 2-benzoylbenzene-1,3-dicarboxylic acid, 1,3-dibenzyl-2-oxoimidazolidine-4,5-cis-dicarboxylic acid, 2,2'-biquinoline-4,4'-dicarboxylic acid, pyridine-3,4-dicarboxylic acid, 3,6,9-trioxaundecanedicarboxylic acid, O-hydroxybenzophenonedicarboxylic acid, Pluriol E 300-dicarboxylic acid, Pluriol E 400-dicarboxylic acid, Pluriol E 600-dicarboxylic acid, pyrazole-3,4-dicarboxylic acid, 2,3-pyrazinedicarboxylic acid, 5,6-dimethyl-2,3-pyrazinedicarboxylic acid, 4,4'-diamino(diphenyl ether)diimidedicarboxylic acid, 4,4'-diaminodiphenylmethanediimidedicarboxylic acid, 4,4'-diamino(diphenyl sulfone)-dimidedicarboxylic acid, 2,6-naphthalenedicarboxylic acid, 1,3-adamantanedicarboxylic acid, 1,8-naphthalenedicarboxylic acid, 2,3-naphthalenedicarboxylic acid, 8-methoxy-2,3-naphthalenedicarboxylic acid, 8-nitro-2,3-naphthalenedicarboxylic acid, 8-sulfo-2,3-naphthalenedicarboxylic acid, anthracene-2,3-dicarboxylic acid, 2',3'-diphenyl-p-terphenyl-4,4"-dicarboxylic acid, (diphenyl ether)-4,4'-dicarboxylic acid, imidazole-4,5-dicarboxylic acid, 4(1H)-oxothiochromene-2,8-dicarboxylic acid, 5-tert-butyl-1,3-benzenedicarboxylic acid, 7,8-quinolinedicarboxylic acid, 4,5-imidazoledicarboxylic acid, 4-cyclohexene-1,2-dicarboxylic acid, hexatriacontanedicarboxylic acid, tetradecanedicarboxylic acid, 1,7-heptanedicarboxylic acid, 5-hydroxy-1,3-benzenedicarboxylic acid, pyrazine-2,3-dicarboxylic acid, furan-2,5-dicarboxylic acid, 1-nonene-6,9-dicarboxylic acid, eicosenedicarboxylic acid, 4,4'-dihydroxydiphenylmethane-3,3'-dicarboxylic acid, 1-amino-4-methyl-9,10-dioxo-9,10-dihydroanthracene-2,3-dicarboxylic acid, 2,5-pyridine-dicarboxylic acid, cyclohexene-2,3-dicarboxylic acid, 2,9-dichlorofluorubin-4,11-dicarboxylic acid, 7-chloro-3-methylquinoline-6,8-dicarboxylic acid, 2,4-dichlorobenzophenone-2',5'-dicarboxylic acid, 1,3-benzenedicarboxylic acid, 2,6-pyridinedicarboxylic acid, 1-methylpyrrole-3,4-dicarboxylic acid, 1-benzyl-1H-pyrrole-3,4-dicarboxylic acid, anthraquinone-1,5-dicarboxylic acid, 3,5-pyrazoledicarboxylic acid, 2-nitrobenzene-1,4-dicarboxylic acid, heptane-1,7-dicarboxylic acid, cyclobutane-1,1-dicarboxylic acid 1,14-tetradecanedicarboxylic acid, 5,6-dehydronorbornane-2,3-dicarboxylic acid or 5-ethyl-2,3-pyridinedicarboxylic acid,
tricarboxylic acids such as
2-hydroxy-1,2,3-propanetricarboxylic acid, 7-chloro-2,3,8-quinolinetricarboxylic acid, 1,2,4-benzenetricarboxylic acid, 1,2,4-butanetricarboxylic acid, 2-phosphono-1,2,4-butanetricarboxylic acid, 1,3,5-benzenetricarboxylic acid, 1-hydroxy-1,2,3-propanetricarboxylic acid, 4,5-dihydro-4,5-di-oxo-1H-pyrrolo[2,3-F]quinoline-2,7,9-tricarboxylic acid, 5-acetyl-3-amino-6-methylbenzene-1,2,4-tricarboxylic acid, 3-amino-5-benzoyl-6-methylbenzene-1,2,4-tricarboxylic acid, 1,2,3-propanetricarboxylic acid or aurintricarboxylic acid,
or tetracarboxylic acids such as
1,1-dioxidoperylo[1,12-BCD]thiophene-3,4,9,10-tetracarboxylic acid, perylenetetracarboxylic acids such as perylene-3,4,9,10-tetracarboxylic acid or perylene-1,12-sulfone-3,4,9,10-tetracarboxylic acid, butanetetracarboxylic acids such as 1,2,3,4-butanetetracarboxylic acid or meso-1,2,3,4-butanetetracarboxylic acid, decane-2,4,6,8-tetracarboxylic acid, 1,4,7,10,13,16-hexaoxacyclooctadecane-2,3,11,12-tetracarboxylic acid, 1,2,4,5-benzenetetracarboxylic acid, 1,2,11,12-dodecanetetracarboxylic acid, 1,2,5,6-hexanetetracarboxylic acid, 1,2,7,8-octane-tetracarboxylic acid, 1,4,5,8-naphthalenetetracarboxylic acid, 1,2,9,10-decanetetracarboxylic acid, benzophenonetetracarboxylic acid, 3,3',4,4'-benzophenonetetracarboxylic acid, tetrahydrofurantetracarboxylic acid or cyclopentanetetracarboxylic acids such as cyclopentane-1,2,3,4-tetracarboxylic acid.

In the process of the invention, very particular preference is given to using unsubstituted or at least monosubstituted dicarboxylic, tricarboxylic or tetracarboxylic acids having one, two, three, four or more rings, with each of the rings being able to comprise at least one heteroatom and two or more rings being able to comprise identical or different heteroatoms. Examples of preferred carboxylic acids of this type are one-ring dicarboxylic acids, one-ring tricarboxylic acids, one-ring tetracarboxylic acids, two-ring dicarboxylic acids, two-ring tricarboxylic acids, two-ring tetracarboxylic acids, three-ring dicarboxylic acids, three-ring tricarboxylic acids, three-ring tetracarboxylic acids, four-ring dicarboxylic acids, four-ring tricarboxylic acids and/or four-ring tetracarboxylic acids. Suitable heteroatoms are, for example, N, O, S, B, P, Si, Al, and preferred heteroatoms are N, S and/or O, Suitable substituents are, inter alia, —OH, a nitro group, an amino group or an alkyl or alkoxy group.

As first organic compounds in the process of the invention, particular preference is given to using acetylenedicarboxylic acid (ADC), benzenedicarboxylic acids, naphthalenedicarboxylic acids, biphenyldicarboxylic acids such as 4,4'-biphenyldicarboxylic acid (BPDC), bipyridinedicarboxylic acids such as 2,2'-bipyridinedicarboxylic acids, e.g. 2,2'-bipyridine-5,5'-dicarboxylic acid, benzenetricarboxylic acids such as 1,2,3-benzenetricarboxylic acid or 1,3,5-benzenetricarboxylic acid (BTC), adamantanetetracarboxylic acid (ATC), adamantanedibenzoate (ADB), benzenetribenzoate (BTB), methanetetrabenzoate (MTB), adamantanetetrabenzoate or dihydroxyterephthalic acids such as 2,5-dihydroxyterephthalic acid (DHBDC).

Very particular preference is given to using, inter alia, terephthalic acid, 2,5-dihydroxyterephthalic acid, 1,2,3-benzenetricarboxylic acid, 1,3,5-benzenetricarboxylic acid or 2,2'-bipyridine-5,5'-dicarboxylic acid for the purposes of the present invention.

Very particular preference is also given to dicarboxylic acids, in particular terephthalic acid, naphthalenedicarboxylic acid, isophthalic acid, biphenylenedicarboxylic acid, p-carboxycinnamic acid, malonic acid, fumaric acid and anthracenedicarboxylic acid.

In a preferred embodiment, terephthalic acid is used as first organic compound. If at least one solvent is used, preference is given to using, for example, dimethylformamide or diethylformamide or dimethylformamide and diethylformamide as solvent. Particular preference is given to diethylformamide.

In a further for example preferred, embodiment, naphthalene-2,6-dicarboxylic acid is used as first organic compound.

If at least one solvent is used, preference is given to using, for example, methanol or ethanol or methanol and ethanol as solvent. Particular preference is given to methanol.

The first organic compound is used in a concentration which is generally in the range from 0.1 to 30% by weight, preferably in the range from 0.5 to 20% by weight and particularly preferably in the range from 2 to 10% by weight, in each case based on the total weight of the reaction system minus the weight of the anode and the cathode. Accordingly, the term "concentration" in this case comprises both the amount of the first organic compound dissolved in the reaction system and, for example, the amount of the first organic compound which may, if appropriate, be suspended in the reaction system.

In a preferred embodiment of the process of the invention, the first organic compound is added continuously and/or discontinuously as a function of the progress of the electrolysis and in particular as a function of the decomposition of the anode or liberation of the at least one metal ion and or as a function of the formation of the metal-organic framework.

The following combinations of metal from which the at least one metal cation is provided by means of anodic oxidation, first organic compound and solvent are, for example, preferred for the purposes of the present invention:
Zn/BDC/DEF; Zn/DHBDC/DEF; Zn/H$_2$BDC/DMF; Zn/BDC/DMF, MeOH;
Zn/H$_2$BDC/DMF; Zn/4,4'-BP-2,2'-DC/DEF; Zn/2,6-NDC/DEF;
Zn/H$_3$BTB/H$_2$O,DMF,EtOH; Zn/H$_2$BDC/DMSO; Zn/1,4-NDC/DMF;
Zn/H$_3$BTB/DMF,EtOH; Zn/H$_2$BDC/DMF,AN; Zn/H$_2$BDC/DMSO;
Zn/H$_2$BDC/DMSO,MeOH; Zn/H$_2$BDC/DMSO,n-propanol; Zn/H$_2$BDC/NMP;
Zn/m-BDC/DMF,AN; Zn/1,4-NDC/DMF,EtOH; Zn/H$_2$N-BDC/DEF,EtOH;
Zn/1,4-NDC/DEF; Zn/2,6-NDC/DEF; Zn/PDC/DEF;
Cu/BDC/DEF; Cu/1,3,5-BTC/EtOH; Cu/1,2,3-BTC/MeOH; Cu/H$_3$BTB/H$_2$O,DMF,EtOH;
Cu/H$_2$BDC(OH)$_2$/DMF; Cu/thiophenedicarboxylic acid/DEF;
Cu/thiophenedicarboxylic acid/DMF; Cu/thiophenedicarboxylic acid/MeOH;
Cu/malonic acid/DMF; Cu/glutaric acid/DMF; Cu/tartaric acid/DMF;
Fe/H$_2$BDC/DMF; Fe/H$_3$BDC/DMF; Fe/BTC/DMF; Fe/BDC/DMF, EtOH;
Fe/BPDC/DMF,n-propanol; Fe/m-BDC/pyridine; Fe/m-BDC/DMF, pyridine;
Co/BDC/MeOH; Co/H$_2$BDC/NMP; Co/H$_2$BDC/DMF
Mg/BDC/DEF; Mg/BDC(OH)$_2$/DMF;
Pb/H$_2$BDC/DMF, EtOH.

Here, the following abbreviations apply:

| | |
|---|---|
| BDC | benzenedicarboxylic acid |
| m-BDC | m-benzenedicarboxylic acid |
| H$_2$BDC | dihydroterephthalic acid |
| H$_2$N-BDC | aminoterephthalic acid |
| 4,4'-BP-2,2'-DC | 4,4'-biphenyl-2,2'-dicarboxylic acid |
| 4,4'-BPDC | 4,4'-biphenyldicarboxylic acid |
| H$_3$BTB | benzenetribenzoate |
| 1,3,5-BTC | 1,3,5-benzenetricarboxylic acid |
| 1,2,3-BTC | 1,2,3-benzenetricarboxylic acid |
| DHBDC | 2,5-dihydroxyterephthalic acid |
| 2,6-NDC | 2,6-naphthalenedicarboxylic acid |

| | |
|---|---|
| 1,4-NDC | 1,4-naphthalenedicarboxylic acid |
| PDC | pyrenedicarboxylic acid |

When the process of the invention is carried out as a "single-step synthesis", these combinations are likewise preferred, with a second organic compound as explained in more detail below being additionally employed.

In a particularly preferred embodiment of step a) or the "single-step synthesis" of the process of the invention, the reaction medium comprises at least one suitable electrolyte salt. Depending on the first organic compound used and/or the solvent which may be used if appropriate, it is also possible, in the process of the invention, to carry out the preparation of the intermediate complex without an additional electrolyte salt.

The electrolyte salts which can be used in the process of the invention for step a) or for the "single-step synthesis" are subject to essentially no restrictions. Preference is given to using, for example, salts of mineral acids, sulfonic acids, phosphonic acids, boronic acids, alkoxysulfonic acids or carboxylic acids or other acidic compounds such as sulfonamides or imides.

Possible anionic components of the at least one electrolyte salt are accordingly, inter alia, sulfate, nitrate, nitrite, sulfite, disulfite, phosphate, hydrogenphosphate, dihydrogenphosphate, diphosphate, triphosphate, phosphite, chloride, chlorate, bromide, bromate, iodide, iodate, carbonate or hydrogencarbonate.

Possible cation components of the electrolyte salts which can be used according to the invention are, inter alia, alkali metal ions such as $Li^+$, $Na^+$, $K^+$ or $Rb^+$, alkaline earth metal ions such as $Mg^{2+}$, $Ca^{2+}$, $Sr^{2+}$ or $Ba^{2+}$, ammonium ions or phosphonium ions.

Among the ammonium ions, quaternary ammonium ions and protonated monoamines, diamines and triamines may be mentioned.

Examples of quaternary ammonium ions which are preferably used according to the invention in step a) or for the "single-step synthesis" of the process of the invention are, inter alia, symmetrical ammonium ions such as tetraalkylammonium preferably bearing $C_1$-$C_4$-alkyl, for example methyl, ethyl, n-propyl, isopropyl, n-butyl, isobutyl, tert-butyl, e.g. tetramethylammonium, tetraethylammonium, tetrapropylammonium, tetrabutylammonium, or unsymmetrical ammonium ions such as unsymmetrical tetraalkylammonium preferably bearing $C_1$-$C_4$-alkyl, for example methyl, ethyl, n-propyl, isopropyl, n-butyl, isobutyl, tert-butyl, e.g. methyltributylammonium, or ammonium ions bearing at least one aryl, for example phenyl or naphthyl, or at least one alkaryl, for example benzyl, or at least one aralkyl and at least one alkyl, preferably $C_1$-$C_4$-alkyl, for example methyl, ethyl, n-propyl, isopropyl, n-butyl, isobutyl, tert-butyl, e.g. aryltrialkyl, e.g. benzyltrimethylammonium or benzyltriethylammonium.

In a particularly preferred embodiment, at least one electrolyte salt which comprises a methyltributylammonium ion as at least one cationic component is used in the process of the invention.

In a particularly preferred embodiment, methyltributylammonium methylsulfate is used as electrolyte salt in step a) or the "single-step synthesis" in the process of the invention.

Ionic liquids such as methylethylimidazolium chloride or methylbutylimidazolium chloride can also be used as electrolyte salts in the process of the invention.

In a likewise preferred embodiment, methanesulfonate is used as electrolyte salt in the process of the invention.

As cation component of the at least one electrolyte salt, mention may also be made according to the invention of protonated or quaternary heterocycles such as the imidazolium ion.

In a preferred embodiment of the process of the invention, compounds which are used for the formation of the intermediate complex can be introduced into the reaction medium via the cationic and/or anionic component of the at least one electrolyte salt. These compounds are compounds which influence the formation of the structure of the intermediate complex but are not comprised in the resulting intermediate and also compounds which are comprised in the resulting intermediate. In particular, at least one compound which is comprised in the resulting intermediate complex can be introduced via at least one electrolyte salt in the process of the invention.

Preference is given, for example, in this respect to, inter alia, tetraalkylammonium carboxylate such as a monotetraalkylammonium salt of 1,3,5-benzenetricarboxylic acid. In this embodiment, preference is given, inter alia, to using 1,3,5-benzenetricarboxylic acid together with tetraalkylammonium hydroxide in methanol as solvent. This method of carrying out the process offers, inter alia, the advantage that tetraalkylammonium hydroxide is generally used as an aqueous solution and water thus automatically becomes an essential constituent of the reaction medium.

The present invention accordingly also provides a process as described above in which at least one compound required for forming the metal-organic framework, preferably at least one compound comprised in the metal-organic framework to be prepared, is introduced into the reaction system at least partly via at least one electrolyte salt.

In an embodiment of the process of the invention, it is thus possible for the metal ion to be introduced into the reaction medium via the cationic component of the at least one electrolyte salt in addition to the at least one anode as metal ion source in step a) or in the "single-step synthesis". It is likewise possible for at least one metal ion which is different from the at least one metal ion introduced by means of anodic oxidation to be introduced into the reaction medium via the cationic component of the at least one electrolyte salt. In this case, this difference can be in the valence of the cation and/or the type of metal.

It is likewise possible to use salts whose anion component or anion components is/are a compound/compounds used for the formation of the intermediate complex as electrolyte salts in the process of the invention. In particular, use can therefore be made of electrolyte salts whose anion component is, for example, the monocarboxylate or dicarboxylate or tricarboxylate or tetracarboxylate or monosulfonate or disulfonate or trisulfonate or tetrasulfonate, preferably a dicarboxylate or tricarboxylate or tetracarboxylate and more preferably the dicarboxylate or tricarboxylate or tetracarboxylate, of the aromatic dicarboxylic, tricarboxylic or tetracarboxylic acids which are preferably used.

The present invention therefore also provides a process as described above in which the at least one electrolyte salt comprises a salt of the first organic compound.

In the process of the invention, the concentration of the at least one electrolyte salt is generally in the range from 0.01 to 10% by weight, preferably in the range from 0.05 to 5% by weight and particularly preferably in the range from 0.1 to 3% by weight, in each case based on the sum of the weights of all electrolyte salts present in the reaction system and also based on the total weight of the reaction system without taking account of the anodes and cathodes.

If step a) of the process or the "single-step synthesis" is carried out in the batch mode, the reaction medium comprising the starting materials is generally firstly provided, current is subsequently applied and the reaction mixture is then circulated by pumping.

If the process is carried out continuously, a substream is generally discharged from the reaction medium, the intermediate complex comprised therein is isolated and the mother liquor is returned.

In a particularly preferred embodiment, step a) or the "single-step synthesis" of the process of the invention is carried out so that the redeposition of the metal ion liberated by anodic oxidation on the cathode is prevented.

According to the invention, this redeposition is preferably prevented by, for example, using a cathode which has an appropriate hydrogen overvoltage in a given reaction medium. Such cathodes are, for example, the abovementioned graphite, copper, zinc, tin, manganese, silver, gold, platinum cathodes or cathodes comprising alloys such as steels, bronzes or brass.

According to the invention, the redeposition is preferably also prevented by, for example, an electrolyte which favors the cathodic formation of hydrogen being used in the reaction medium. In this case, preference is given, inter alia, to an electrolyte which comprises at least one protic solvent. Preferred examples of such solvents have been given above. Particular preference is given to alcohols, in particular methanol and ethanol.

According to the invention, the redeposition is preferably also prevented by, for example, at least one compound which leads to cathodic depolarization being comprised in the reaction medium. For the purposes of the present invention, a compound which leads to cathodic depolarization is any compound which is reduced at the cathode under the given reaction conditions.

Preferred cathodic depolarizers are, inter alia, compounds which are hydrodimerized at the cathode. Examples of compounds which are particularly preferred in this context are acrylonitrile, acrylic esters and maleic esters such as, more preferably, dimethyl maleate.

As cathodic depolarizers, preference is also given, inter alia, to compounds which comprise at least one carbonyl group which is reduced at the cathode. Examples of such compounds comprising carbonyl groups are esters such as dialkyl phthalate and ketones such as acetone.

As cathodic depolarizers, preference is given, inter alia, to compounds which have at least one nitrogen-oxygen bond, a nitrogen-nitrogen bond and/or a nitrogen-carbon bond which is/are reduced at the cathode. Examples of such compounds are compounds having a nitro group, compounds having a azo group, compounds having an azoxy group, oximes, pyridines, imines, nitrites and/or cyanates.

In the process of the invention, it is also possible to combine at least two of the abovementioned measures for preventing cathodic redeposition. For example, it is possible both to use an electrolyte which favors the cathodic formation of hydrogen and also to use an electrode having an appropriate hydrogen overvoltage. It is likewise possible both to use an electrolyte which favors the cathodic formation of hydrogen and to add at least one compound which leads to cathodic depolarization. It is likewise possible both to add at least one compound which leads to cathodic depolarization and to use a cathode having an appropriate hydrogen overvoltage. It is also possible both to use an electrolyte which favors the cathodic formation of hydrogen and to use an electrode having an appropriate hydrogen overvoltage and also to add at least one compound which leads to cathodic depolarization.

Accordingly, the present invention also provides a process as described above in which cathodic redeposition of the at least one metal ion in step a) or in the "single-step synthesis" is at least partly prevented by means of at least one of the following measures:
(i) use of an electrolyte which favors cathodic formation of hydrogen;
(ii) addition of at least one compound which leads to cathodic depolarization;
(iii) use of a cathode having an appropriate hydrogen overvoltage.

The present invention therefore likewise provides a process as described above in which the electrolyte according to (i) comprises at least one protic solvent, in particular an alcohol, more preferably methanol and/or ethanol.

The present invention therefore likewise provides a process as described above in which the cathodic depolarization is a hydrodimerization, in particular a hydrodimerization of a maleic diester, more preferably of dimethyl maleate.

In particular, the present invention relates to a process as described above in which both at least one protic solvent, preferably an alcohol, more preferably methanol or ethanol or a mixture of methanol and ethanol, and at least one compound capable of cathodic hydrodimerization, preferably a maleic diester and more preferably dimethyl maleate, are used to prevent redeposition.

In a particularly preferred embodiment, the process of the invention is operated in the circulation mode for step a) or for the "single-step synthesis". For the purposes of the present invention, this "electrolysis circuit" refers to any process configuration in which at least part of the reaction system present in the electrolysis cell is discharged from the electrolysis cell, if appropriate subjected to at least one intermediate treatment step such as at least one thermal treatment or addition and/or removal of at least one component from the discharged stream and returned to the electrolysis cell. For the purposes of the present invention, such an electrolysis circuit is particularly preferably operated in combination with a plate stack cell, a tube cell or a pencil sharpener cell.

After the preparation is complete, the generally crystalline porous intermediate complex in the case of the two-stage synthesis is generally present in the form of primary crystals in the mother liquor.

After the preparation of the intermediate complex is complete, the framework solid of the intermediate complex can be separated off from its mother liquor. This separation step can in principle be carried out by means of any suitable method. The intermediate is preferably separated off by solid-liquid separation, centrifugation, extraction, filtration, membrane filtration, crossflow filtration, diafiltration, ultrafiltration, flocculation using flocculants such as nonionic, cationic and/or anionic auxiliaries, pH shift by addition of additives such as salts, acids or bases, flotation, spray drying, spray granulation or evaporation of the mother liquor at elevated temperatures and/or under reduced pressure and concentration of the solid.

The separation can be followed by at least one additional washing step, at least one additional drying step and/or at least one additional calcination step.

If step a) of the process of the invention is followed by at least one washing step, washing is preferably carried out using at least one solvent used in the synthesis.

If step a) of the process of the invention is followed, if appropriate after at least one washing step, by at least one drying step, the framework solid is generally dried at temperatures in the range from 20 to 120° C., preferably in the range from 40 to 100° C. and particularly preferably in the range from 56 to 60° C.

Preference is likewise given to drying under reduced pressure, with the temperatures generally being able to be selected so that the at least one washing liquid is at least partly, preferably essentially completely, removed from the crystalline porous metal-organic framework and the framework structure is at the same time not destroyed.

The drying time is generally in the range from 0.1 to 15 hours, preferably in the range from 0.2 to 5 hours and particularly preferably in the range from 0.5 to 1 hour.

The optionally at least one washing step and optionally at least one drying step in step a) can be followed by at least one calcination step in which the temperatures are preferably selected so that the structure of the framework is not destroyed.

Washing and or drying and/or calcination, in particular, make it possible, for example, to achieve at least partial, preferably essentially quantitative, removal of a template compound which may have been used, if appropriate, for the electrochemical preparation of the framework according to the invention.

As indicated above, in step b) of the process of the invention, either the intermediate complex is, without being isolated first, reacted with a second organic compound or the intermediate is separated off and reacted with the second organic compound, preferably in a solvent. This reaction is typically carried out in the same way as classical methods of preparation for porous metal-organic frameworks (i.e. not electrochemically).

The reaction in step b) is preferably carried out in a solvent or solvent mixture. Here, it is possible to use liquid phases as can be used for step a) of the process of the invention. Apart from the intermediate complex and the second organic compound, further additives can participate in the reaction.

The isolation and further optional steps of the metal-organic framework formed in step b) can be carried out in the same way as described for the intermediate complex from step a). Likewise, the isolation and further optional steps of the metal-organic framework of the invention can in the case of the "single-step synthesis" be carried out as in step a) of the two-stage synthesis.

The reaction in step b) is preferably carried out at a temperature in the range from 50° C. to 200° C. The temperature is more preferably in the range from 100° C. to 200° C.

The second organic compound comprises at least one heteroatom selected from the group consisting of N, O, S and halogen, with N, O, S being able to be present as amine, imine, diazo, alcohol, ether, keto, aldehyde, peroxo, thiol, thioether or disulfide groups.

The second organic compound is preferably a monocyclic, bicyclic or polycyclic saturated or unsaturated hydrocarbon in which at least one ring carbon has been replaced by a heteroatom selected from the group consisting of N, O and S.

The hydrocarbon can be unsubstituted or substituted. If more than one substituent is present, the substituents can be identical or different. Substituents can each be, independently of one another, amino, hydroxy, thio, halogen, pseudohalogen, keto, formyl, amide or an aliphatic branched or unbranched saturated or unsaturated hydrocarbon having from 1 to 4 carbon atoms. If the substituents comprise one or more hydrogen atoms, each of these can, independently of one another, also be replaced by an aliphatic branched or unbranched saturated or unsaturated hydrocarbon having from 1 to 4 carbon atoms.

Halogen can be fluorine, chlorine, bromine or iodine. Pseudohalogen is, for example, cyano, cyanato or isocyanato.

An aliphatic branched or unbranched saturated or unsaturated hydrocarbon having from 1 to 4 carbon atoms is, for example, methyl, ethyl, n-propyl, i-propyl, n-butyl, i-butyl, t-butyl, vinyl, ethynyl or allyl.

The monocyclic, bicyclic or polycyclic hydrocarbon preferably has 5- or 6-membered rings, more preferably 6-membered rings.

Furthermore, preference is given to the at least one heteroatom being nitrogen.

Preference is likewise given to the second organic compound having at least two heteroatoms.

Furthermore, the second organic compound preferably has precisely two heteroatoms, preferably nitrogen.

When the hydrocarbon has a 6-membered ring in which two heteroatoms, preferably nitrogen, are present, these are preferably located in the para position relative to one another.

It is also preferred that the second organic compound is derived from an unsaturated hydrocarbon which is aromatic or fully saturated. If the second organic compound has more than one ring, it is preferred that at least one ring is aromatic.

The monocyclic hydrocarbon from which the second organic compound is derived is, for example, cyclobutane, cyclobutene, cyclobutadiene, pentane, pentene, pentadiene, benzene, cyclohexane or cyclohexene. The monocyclic hydrocarbon from which the second organic compound is derived is preferably benzene or cyclohexane.

The bicyclic hydrocarbon from which the second organic compound is derived can, for example, comprise two rings which are linked to one another via a covalent single bond or via a group R.

R can be —O—, —NH—, —S—, —OC(O)—, —NHC(O)—, —N=N— or an aliphatic branched or unbranched saturated or unsaturated hydrocarbon which has from 1 to 4 carbon atoms and may be interrupted by one atom or functional group or independently by a plurality of atoms or functional groups selected from the group consisting of —O—, —NH—, —S—, —OC(O)—, —NHC(O)— and —N=N—.

Examples of a bicyclic hydrocarbon from which the second organic compound is derived and which comprises two rings which are linked to one another via a covalent single bond or via a group R are biphenyl, stilbene, diphenyl ether, N-phenylbenzamide and azobenzene. Preference is given to biphenyl.

Furthermore, the bicyclic hydrocarbon from which the second compound is derived can be a fused ring system.

Examples of such hydrocarbons are decalin, tetralin, naphthalene, indene, indane, pentalene. Preference is given to tetralin and naphthalene.

Furthermore, the bicyclic hydrocarbon from which the second organic compound is derived can have a bridged ring system.

Examples of such hydrocarbons are bicyclo[2.2.1]heptane and bicyclo[2.2.2]octane, with the latter being preferred.

The polycyclic hydrocarbon from which the second organic compound is derived can likewise comprise fused and/or bridged ring systems.

Examples of such hydrocarbons are biphenylene, indacene, fluorene, phenalene, phenanthrene, anthracene, naphthacene, pyrene, crysene, triphenylene, 1,4-dihydro-1,4-ethanonaphthalene and 9,10-dihydro-9,10-ethanoanthracene. Preference is given to pyrene, 1,4-dihydro-1,4-ethanonaphthalene and 9,10-dihydro-9,10-ethanoanthracene.

Ring systems which are particularly preferred as second organic compound are imidazole and:

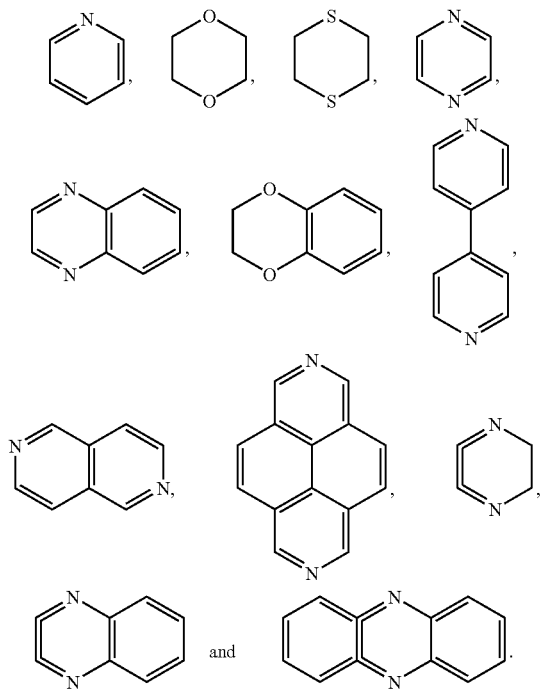

The present invention further provides a porous metal-organic framework which is obtainable from the process of the invention.

The crystalline porous metal-organic framework from step b) or from the "single-step synthesis" is generally obtained as a fine powder in which the crystals have a size in the range from 0.1 to 300 μm, determined by means of SEM (scanning electron microscopy).

The pore sizes of the porous metal-organic frameworks prepared according to the invention can be set within a wide range via the type and number of the first, second and, if appropriate, further organic compounds and/or the type and, if appropriate, oxidation state of the at least one metal ion.

It is accordingly possible for the framework prepared according to the invention to comprise micropores or mesopores or macropores or micropores and mesopores or micropores and macropores or mesopores and macropores or micropores and mesopores and macropores. The frameworks prepared according to the invention particularly preferably comprise micropores or mesopores or micropores and mesopores. The term "micropores" as used for the purposes of the present invention refers to pores having a diameter of up to 2 nm. The term "mesopores" as used for the purposes of the present invention refers to pores having a diameter of from >2 nm to 50 nm. These definitions correspond to the definitions given in Pure Appl. Chem. 45 (1976), p. 71 ff., in particular p. 79. The presence of micropores and or mesopores can be determined by nitrogen adsorption measurements at 77 K in accordance with DIN 66131 and DIN 66135 and DIN 66134.

The present invention accordingly also provides a framework as described above comprising micropores or mesopores or both micropores and mesopores.

The specific surface area of the crystalline porous metal-organic frameworks prepared according to the invention, determined in accordance with DIN 66135, is generally at least 5 $m^2/g$, in particular greater than 5 $m^2/g$, more preferably at least 10 $m^2/g$, in particular greater than 10 $m^2/g$, more preferably at least 50 $m^2/g$, in particular greater than 50 $m^2/g$, more preferably at least 100 $m^2/g$, in particular greater than 100 $m^2/g$, more preferably at least 250 $m^2/g$, in particular greater than 250 $m^2/g$, more preferably at least 500 $m^2/g$, in particular greater than 500 $m^2/g$, with the specific surface area being able to be up to more than 1000 $m^2/g$, for example greater than 2000 $m^2/g$, as a further example greater than 3000 $m^2/g$ and as a particular example greater than 4000 $m^2/g$.

The term "specific surface area" as used for the purposes of the present invention refers to the surface area determined according to the Langmuir model at 77 K in accordance with DIN 66135.

The present invention accordingly also provides a metal-organic framework as described above which has a specific surface area determined in accordance with DIN 66135 of greater than or equal to 500 $m^2/g$, preferably greater than or equal to 1000 $m^2/g$ and particularly preferably greater than or equal to 1250 $m^2/g$.

In a further embodiment of the process of the invention, the porous metal-organic framework which has been separated off from the mother liquor is shaped to produce one or more shaped bodies.

The possible geometries of these shaped bodies are subject to essentially no restrictions. Examples are, inter alia, pellets such as disk-shaped pellets, pills, spheres, granules, extrudates such as rod extrudates, honeycombs, grids and hollow bodies.

All suitable processes are in principle possible for producing these shaped bodies. Preferred processes for producing shaped bodies are disclosed in US 2003/0222023 A1 and the U.S. patent application Ser. No. 10/983,629. For the purposes of the present invention, the following processes, inter alia, are preferred:

kneading of the framework either alone or together with at least one binder and or at least one pasting agent and/or at least one template compound to give a mixture;

shaping of the resulting mixture by means of at least one suitable method, for example extrusion;

optionally washing and/or drying and or calcination of the extrudate;

optionally finishing.

Application of the framework to at least one optionally porous support material. The material obtained can then be processed further by the method described above to give a shaped body.

Application of the framework to at least one optionally porous substrate.

Kneading and shaping can be carried out by any suitable method, as described, for example, in Ullmanns Enzyklopädie der Technischen Chemie, 4th edition, Volume 2, p. 313 ff. (1972), whose relevant contents are fully incorporated by reference into the present patent application.

For example, the kneading and/or shaping can preferably be carried out by means of a piston press, roll press in the present or absence of at least one binder material, compounding, pelletization, tableting, extrusion, coextrusion, foaming, spinning, coating, granulation, preferably spray granulation, spraying, spray drying or a combination of two or more of these methods.

Pellets and/or tablets are very particularly produced in the process of the invention.

The kneading and/or shaping can be carried out at elevated temperatures, for example in the range from room temperature to 300° C., and or at elevated pressure, for example in the range from atmospheric pressure to a few hundred bar, and/or in a protective gas atmosphere, for example in the presence of at least one noble gas, nitrogen or a mixture of two or more thereof.

The kneading and/or shaping is, according to a further embodiment of the process of the invention, carried out with addition of at least one binder, with the binder used being able in principle to be any chemical compound which ensures the desired viscosity for kneading and/or shaping the composition. Accordingly, binders can, for the purposes of the present invention, be either viscosity-increasing or viscosity-reducing compounds.

Preferred binders include, for example, aluminum oxide or binders comprising aluminum oxide as described, for example, in WO 94/29408, silicon dioxide as described, for example, in EP 0 592 050 A1, mixtures of silicon dioxide and aluminum oxide as described, for example, in WO 94/13584, clay minerals as described, for example, in JP 03-037156 A, for example montmorillonite, kaolin, bentonite, hallosite, dickite, nacrite and anauxite, alkoxysilanes as described, for example, in EP 0 102 544 B1, for example tetraalkoxysilanes such as tetramethoxysilane, tetraethoxysilane, tetrapropoxysilane, tetrabutoxysilane, and, for example, trialkoxysilanes such as trimethoxysilane, triethoxysilane, tripropoxysilane, tributoxysilane, alkoxytitanates, for example tetraalkoxytitanates such as tetramethoxytitanate, tetraethoxytitanate, tetrapropoxytitanate, tetrabutoxytitanate, and, for example, trialkoxytitanates such as trimethoxytitanate, triethoxytitanate, tripropoxytitanate, tributoxytitanate, alkoxyzirconates, for example tetraalkoxyzirconates such as tetramethoxyzirconate, tetraethoxyzirconate, tetrapropoxyzirconate, tetrabutoxyzirconate, and, for example, trialkoxyzirconates such as trimethoxyzirconate, triethoxyzirconate, tripropoxyzirconate, tributoxyzirconate, silica sols, amphiphilic substances and/or graphites. Particular preference is given to graphite.

As viscosity-increasing compound, it is also possible, for example, to use, if appropriate in addition to the above-mentioned compounds, an organic compound and/or a hydrophilic polymer such as cellulose or a cellulose derivative such as methylcellulose and/or a polyacrylate and/or a polymethacrylate and/or a polyvinyl alcohol and/or a polyvinylpyrrolidone and/or a polyisobutene and/or a polytetrahydrofuran.

As pasting agent, preference is given to using, inter alia, water or at least one alcohol, for example a monoalcohol having from 1 to 4 carbon atoms, e.g. methanol, ethanol, n-propanol, isopropanol, 1-butanol, 2-butanol, 2-methyl-1-propanol or 2-methyl-2-propanol, or a mixture of water and at least one of the alcohols mentioned or a monohydric alcohol such as a glycol, preferably a water-miscible polyhydric alcohol, either alone or as a mixture with water and/or at least one of the monohydric alcohols mentioned.

Further additives which can be used for kneading and/or shaping are, inter alia, amines or amine derivatives such as tetraalkylammonium compounds or amino alcohols and carbonate-comprising compounds such as calcium carbonate. Such further additives are described, for instance, in EP 0 389 041 A1, EP 0 200 260 A1 or WO 95/19222, whose relevant contents are fully incorporated by reference into the present patent application.

The order of addition of the additives such as template compound, binder, pasting agent, viscosity-increasing substance in shaping and kneading is in principle not critical.

In a further preferred embodiment of the process of the invention, the shaped body obtained by kneading and/or shaping is subjected to at least one drying operation which is generally carried out a temperature in the range from 25 to 300° C., preferably in the range from 50 to 300° C. and particularly preferably in the range from 100 to 300° C. It is likewise possible to carry out drying under reduced pressure or under a protective gas atmosphere or by spray drying.

In a particularly preferred embodiment, at least one of the compounds added as additives is at least partly removed from the shaped body during this drying operation.

In a further embodiment of the process of the invention, the framework is applied to at least one optionally porous material. A porous substrate is preferably used here.

This application is particularly preferably effected by impregnation with a liquid, steeping in a liquid, spraying, deposition from a liquid phase, deposition from the gas phase (vapor deposition), precipitation, coprecipitation, coating.

As optionally porous substrate, preference is given to using aluminum oxide, silica gel, silicates, diatomaceous earths, kaolin, magnesium oxide, activated carbon, titanium dioxide, phosphates and/or zeolites.

If, for example, nonporous substrates are used, it is possible, in a further embodiment of the process of the invention, to produce shell structures as are known from coated catalysts by application of the porous metal-organic framework to a nonporous shaped body.

The present invention accordingly also provides a shaped body comprising at least one porous metal-organic framework as described above and/or a framework obtainable by a process as described above.

Of course, it is also possible in the process of the invention to add at least one suitable pore former in the production of the shaped bodies. Pore formers which can be used in the process of the invention are all compounds which result in a particular pore size, a particular pore size distribution and/or particular pore volumes in the finished shaped body. Pore formers used in the process of the invention are preferably, inter alia, polymeric vinyl compounds such as polystyrene, polyacrylates, polymethacrylates, polyolefins, polyamides and polyesters. Very particularly preferred pore formers are, for instance, compounds which can be removed at least partly, preferably essentially completely, at the calcination temperatures of the process of the invention. In this respect, mention may be made of, for instance, malonic acid, citric acid, formic acid, acetic acid and their salts.

The porous metal-organic frameworks prepared according to the invention and or the shaped bodies which are produced according to the invention and comprise at least one porous meta-organic framework prepared according to the invention can in principle be used in any conceivable way. They are particularly preferably used as pigments or as sensors, as electric conductors or as ionic conductors.

Particular preference is given to applications in which the high specific surface area of the frameworks can be utilized.

Particular preference is given to using the frameworks, if appropriate comprised in a shaped body, for purifying gases and or liquids, as catalysts, for the absorption and/or storage and/or release of liquids and or gases.

Accordingly, the present invention also provides for the use of a porous metal-organic framework as described above or a porous metal-organic framework obtainable by a process as described above for purifying at least one liquid and/or at least one gas or as storage medium for at least one liquid and/or at least one gas.

The use for storing at least one gas, in particular hydrogen, $C_1$-$C_4$-hydrocarbons such as methane, ethane, propane, butane and in particular methane, is particularly preferred.

Particular preference is also given to using the porous metal-organic framework of the invention for storing at least one gas and/or at least one liquid, particularly preferably at least one gas, very particularly preferably for storing methane or hydrogen, in a container under a pressure in the range from 1 to 750 bar, for example preferably in the range from 1 to 150 bar, more preferably in the range from 1 to 80 bar, more preferably in the range from 45 to 80 bar and particularly preferably in the range from 50 to 80 bar, or for example preferably in the range from 45 to 750 bar, more preferably in the range from 45 to 150 bar, more preferably in the range from 50 to 150 bar and particularly preferably in the range from 50 to 80 bar.

Such containers can be used, for example, in the context of a fuel cell as can be used, for example, for the operation of stationary, mobile and or portable applications. Such applications are, for instance, applications for power stations, motor vehicles, goods vehicles, buses, cable-less applications, mobile telephones or laptops or robots, in particular those which are to be independent of stationary energy supplies for reasons of mobility.

This container can in principle have any suitable geometry. Due to the low pressures which are possible according to the invention, containers which deviate from the standard cylindrical geometry and the respective requirements, for example to be able to be adapted to the specific space available in automobile construction, are preferably also possible. As a result, the containers which can be configured variably can be adapted to hollow spaces of an automobile which can otherwise not be utilized and valuable storage and usable space can be gained.

Furthermore, the frameworks prepared by the process of the invention can be used for gas separation. Further uses are for optical or magnetic applications, as active compound, filler or support, in particular catalyst support.

The invention is illustrated by the following example.

EXAMPLES

Example 1

Preparation of a Cu-Terephthalic Acid-TEDA Metal-Organic Framework 47.5 g of diethylformamide, 4.0 g of terephthalic acid, 5.0 g of dimethyl maleate and 1.0 g of methyltributylammonium methylsulfate are weighed into a cylindrical double-walled cell having two copper electrodes (spacing: 1.0 cm; area facing the other electrode: in each case 9.9 cm$^2$) and provided with magnetic stirrer, inert gas flushing and glass condenser and are heated to 60° C. while stirring. This suspension is subsequently electrolyzed at 0.2 amperes for 4 hours. A turquoise suspension has then been formed, and this quickly settles. The resulting precipitate is filtered off in a stream of nitrogen and washed twice with 50 ml of chloroform. The filtercake is transferred in a nitrogen atmosphere to a glass bottle and activated in a high vacuum (until a pressure of about 10$^{-5}$ mbar has been reached). A weight of 5.6 g of Cu terephthalate framework is obtained as intermediate complex.

In the second step, 0.35 g of the electrochemically prepared copper(II) terephthalate framework is added to a solution of 0.2 g of TEDA (TEDA, triethylenediamine, 1,4-diazabicyclo[2.2.2]octane, DABCO] and 0.25 ml of formic acid in 35 ml of methanol and 5 ml of dimethylformamide. The mixture is maintained at 170° C. in a Teflon autoclave for 1 hour The solid is filtered off, washed with 30 ml of methanol and dried at 110° C. in a vacuum drying oven for 2 hours. The yield is 0.3 g of TEDA-modified Cu terephthalate framework.

The specific surface area (calculated from Langmuir isotherms) is determined by means of $N_2$ in accordance with DIN 66135 at 77 K. The electrochemically prepared framework as intermediate complex has a specific surface area of 477 m$^2$/g before reaction with TEDA. The novel framework obtained by the process of the invention has a specific surface area of 1424 m$^2$/g after the reaction.

Example 2

The electrolyte comprising 11.0 g of 1,4-naphthalenedicarboxylic acid, 5.6 g of DABCO (diazabicyclooctane), 17.2 g of MTBS (methyltributylammonium methylsulfate) and 1816.2 g of methanol (MeOH) is introduced into the cell circuit. A conductivity of 1.8 mS/cm is measured.

The cell circuit comprises a tube cell, a glass cooler and a circulation pump. The pump circulates the electrolyte or the resulting suspension at about 700 l/h.

The tube cell comprises a stainless steel tube (length: 55 cm, internal diameter: 5.00 cm) as cathode and a copper rod as anode (length: 55 cm, diameter: 3.7 cm, surface area: 639 cm$^2$). The arrangement in the electrolysis cell ensures, by means of various airtight seals and screw connections, that the electrodes are arranged concentrically and guarantee a homogeneous distance between cathode and anode all around the anode. The electrolyte which is thermostatted to 39° C. is pumped through this annular space.

The cell is operated at a current of 1 A and a cell voltage of 1.4 V for 2 hours (2.0 Ah) to a current input of 1.5 faraday per mol of 1,4-naphthalenedicarboxylic acid.

After electrolysis is complete, the electrolyte is filtered and washed with 2×50 ml of MeOH. The crystalline product is dried at 50° C. and 2 mbar and 10.5 g of $Cu^{II}$ (1,4-naphthalenedicarboxylate)(DABCO)$_{0.5}$ are obtained (yield=100% based on 2 g of copper dissolved from the anode). The surface area is determined by the Langmuir method in accordance with DIN 66135 and is 942 m$^2$/g.

Example 3

The electrolyte comprising 8.5 g of terephthalic acid, 2.8 g of DABCO (diazabicyclooctane), 17.2 g of MTBS (methyltributylammonium methylsulfate) and 1821.5 g of MeOH is introduced into the cell circuit. A conductivity of 1.6 mS/cm is measured.

The cell circuit comprises a tube cell, a glass cooler and a circulation pump. The pump circulates the electrolyte or the resulting suspension at about 700 l/h.

The tube cell comprises a stainless steel tube (length: 55 cm, internal diameter: 5.00 cm) as cathode and a copper rod as anode (length: 55 cm, diameter: 3.7 cm, surface area: 639 cm$^2$). The arrangement in the electrolysis cell ensures, by means of various airtight seals and screw connections, that the electrodes are arranged concentrically and guarantee a homogeneous distance between cathode and anode all around the anode. The electrolyte which is thermostatted to 44° C. is pumped through this annular space.

The cell is operated at a current of 1 A and a cell voltage of 1.2-1.8 V for 2 hours (2.0 Ah) to a current input of 1.5 faraday per mol of terephthalic acid.

After electrolysis is complete, the electrolyte is filtered and washed with MeOH. The crystalline product is dried at 50° C.

and 2 mbar and 9.9 g of $Cu^{II}$(terephthalate)(DABCO)$_{0.5}$ are obtained (yield=77% based on 3 g of copper dissolved from the anode). The surface area is determined by the Langmuir method in accordance with DIN 66135 and is 2055 m²/g.

The invention claimed is:

1. A process for preparing a porous metal-organic framework comprising at least two organic compounds coordinated to at least one metal ion, which comprises:
   oxidation of at least one anode comprising metal corresponding to the at least one metal ion in the presence of a first and a second organic compound in a reaction medium, with the first organic compound having at least two carboxylate groups and the at least two organic compounds coordinating to the at least one metal ion.

2. The process according to claim 1, wherein the at least one metal is selected from the group consisting of Cu, Ni, Co, Zn, Fe, Ru, Mo, Cr, Mn, W, Rh and Pd.

3. The process according to claim 1, wherein the first organic compound is a dicarboxylic acid.

4. The process according to claim 3, wherein the dicarboxylic acid is selected from the group consisting of terephthalic acid, naphthalenedicarboxylic acid, isophthalic acid, biphenylenedicarboxylic acid, p-carboxycinnamic acid, malonic acid, fumaric acid and anthracenedicarboxylic acid.

5. The process according to claim 1, wherein the second organic compound comprises at least one heteroatom selected from the group consisting of N, O, S and halogen, with N, O, S being able to be present as amine, imine, diazo, alcohol, ether, keto, aldehyde, peroxo, thiol, thioether or disulfide groups.

6. The process according to claim 1, wherein the second organic compound is a monocyclic, bicyclic or polycyclic saturated or unsaturated hydrocarbon in which at least one ring carbon has been replaced by a heteroatom selected from the group consisting of N, O and S.

7. The process according to claim 6, wherein the second organic compound is selected from the group consisting of imidazole,

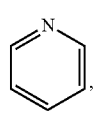, 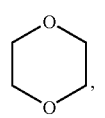, 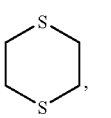, 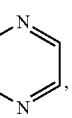,

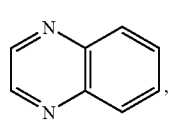, 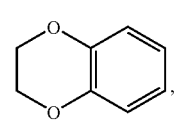, 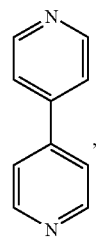,

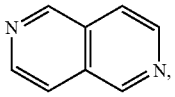, 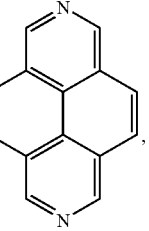, ,

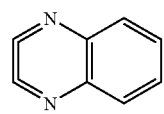 and 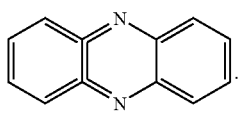.

8. A process for preparing a porous metal-organic framework comprising at least two organic compounds coordinated to at least one metal ion, which comprises:
   a) oxidation of at least one anode comprising metal corresponding to the at least one metal ion in the presence of a first organic compound having at least two carboxylate groups which coordinate to the at least one metal ion in a reaction medium to form an intermediate complex comprising the at least one metal ion and the first organic compound; and
   b) reaction of the intermediate complex at a prescribed temperature with a second organic compound which coordinates to the at least one metal ion.

9. The process according to claim 8, wherein the at least one metal is selected from the group consisting of Cu, Ni, Co, Zn, Fe, Ru, Mo, Cr, Mn, W, Rh and Pd.

10. The process according to claim 8, wherein the first organic compound is a dicarboxylic acid.

11. The process according to claim 10, wherein the dicarboxylic acid is selected from the group consisting of terephthalic acid, naphthalenedicarboxylic acid, isophthalic acid, biphenylenedicarboxylic acid, p-carboxycinnamic acid, malonic acid, fumaric acid and anthracenedicarboxylic acid.

12. The process according to claim 8, wherein the second organic compound comprises at least one heteroatom selected from the group consisting of N, O, S and halogen, with N, O, S being able to be present as amine, imine, diazo, alcohol, ether, keto, aldehyde, peroxo, thiol, thioether or disulfide groups.

13. The process according to claim 8, wherein the second organic compound is a monocyclic, bicyclic or polycyclic saturated or unsaturated hydrocarbon in which at least one ring carbon has been replaced by a heteroatom selected from the group consisting of N, O and S.

14. The process according to claim 13, wherein the second organic compound is selected from the group consisting of imidazole,

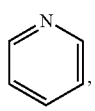, 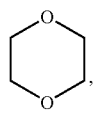, 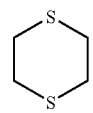, 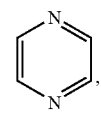,

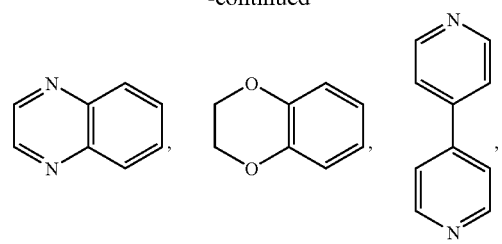
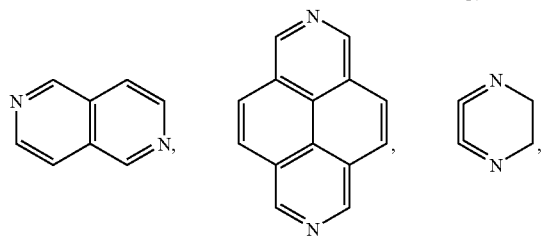
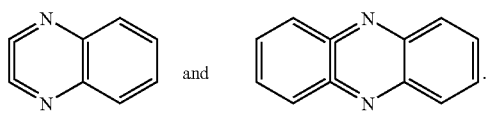
15. The process according to claim 8, wherein the set temperature is in the range from 50° C. to 200° C.
* * * * *